(12) United States Patent
Angelucci et al.

(10) Patent No.: US 10,188,437 B2
(45) Date of Patent: Jan. 29, 2019

(54) SPINE STABILIZATION

(71) Applicant: GLOBUS MEDICAL, INC., Audubon, PA (US)

(72) Inventors: Christopher Angelucci, Schwenksville, PA (US); Michael Black, Phoenixville, PA (US); Brian Garvey, Media, PA (US); James Himmelberger, Souderton, PA (US); Colm McLaughlin, Glenside, PA (US); Robert W. Trout, Spring City, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/461,752

(22) Filed: Mar. 17, 2017

(65) Prior Publication Data

US 2017/0189087 A1 Jul. 6, 2017

Related U.S. Application Data

(63) Continuation of application No. 14/749,897, filed on Jun. 25, 2015, now Pat. No. 9,629,672, which is a continuation of application No. 13/086,122, filed on Apr. 13, 2011, now Pat. No. 9,095,387.

(51) Int. Cl.
*A61B 17/80* (2006.01)
*A61B 17/70* (2006.01)

(52) U.S. Cl.
CPC ...... *A61B 17/8004* (2013.01); *A61B 17/7059* (2013.01); *A61B 17/8009* (2013.01); *A61B 17/8023* (2013.01)

(58) Field of Classification Search
CPC ............ A61B 17/7059; A61B 17/8009; A61B 17/8004; A61B 17/8023
See application file for complete search history.

(56) References Cited

U.S. PATENT DOCUMENTS

| 5,616,142 | A | 4/1997 | Yuan |
| 5,700,263 | A | 12/1997 | Schendel |
| 5,827,286 | A | 10/1998 | Incavo et al. |
| 6,183,476 | B1 | 2/2001 | Gerhardt et al. |
| 6,306,136 | B1 | 10/2001 | Baccelli |
| 6,328,738 | B1 | 12/2001 | Suddaby |
| 6,645,208 | B2 | 11/2003 | Apfelbaum et al. |

(Continued)

*Primary Examiner* — David Bates

(57) ABSTRACT

A bone stabilizing plate includes two plate portions, each affixable to bones of a patient, the plate portions telescoping together with mating rails and grooves. A limiter associated with one of the plate portions sliding engages one a catch associated with the other of the plate portions, when the plate portions are telescoped together, and resists stops telescoping when the plate portions are telescoped a predetermined distance apart. Once the limiter and catch are engaged, the plate portions enable imposition of a minimum compressive force between bones connected to the plates. The limiter is resiliently positioned to deflect into a relief formed in its respective plate portion. A groove positioned proximate the catch enables free telescoping motion limited by the engagement of the catch and limiter, whereby the minimum compressive force between bones is maintained, and Wolfe's Law may apply.

18 Claims, 11 Drawing Sheets

(56) References Cited

U.S. PATENT DOCUMENTS

| | | |
|---|---|---|
| 6,689,134 B2 | 2/2004 | Ralph et al. |
| 6,712,818 B1 | 3/2004 | Michelson |
| 6,719,759 B2 | 4/2004 | Wagner et al. |
| 6,743,255 B2 | 6/2004 | Ferree |
| 6,852,113 B2 | 2/2005 | Nathanson et al. |
| 6,932,820 B2 | 8/2005 | Osman |
| 7,008,427 B2 | 3/2006 | Sevrain |
| 7,041,105 B2 | 5/2006 | Michelson |
| 7,044,952 B2 | 5/2006 | Michelson |
| 7,074,221 B2 | 7/2006 | Michelson |
| 7,097,645 B2 | 8/2006 | Michelson |
| 7,112,202 B2 | 9/2006 | Michelson |
| 7,115,130 B2 | 10/2006 | Michelson |
| 7,118,573 B2 | 10/2006 | Michelson |
| 7,186,254 B2 | 3/2007 | Dinh |
| 7,186,256 B2 | 3/2007 | Michelson |
| 7,214,226 B2 | 5/2007 | Alleyne |
| 7,318,825 B2 | 1/2008 | Butler et al. |
| 7,326,212 B2 | 2/2008 | Huebner |
| 7,331,961 B2 | 2/2008 | Abdou |
| 7,399,301 B2 | 7/2008 | Michelson |
| 7,419,499 B2 | 9/2008 | Dalton |
| 7,547,306 B2 | 6/2009 | Michelson |
| 7,635,364 B2 | 12/2009 | Barrall et al. |
| 7,635,366 B2 | 12/2009 | Abdou |
| 7,645,295 B2 | 1/2010 | Osman |
| 7,727,265 B2 | 6/2010 | Paul |
| 7,763,056 B2 | 7/2010 | Dalton |
| 2003/0187509 A1 | 4/2003 | Lemole |
| 2003/0229348 A1 | 12/2003 | Sevrain |
| 2004/0006343 A1 | 1/2004 | Sevrain |
| 2004/0019353 A1 | 1/2004 | Freid et al. |
| 2004/0092939 A1 | 5/2004 | Freid et al. |
| 2004/0204712 A1 | 10/2004 | Kolb et al. |
| 2005/0010227 A1 | 1/2005 | Paul |
| 2005/0049595 A1 | 3/2005 | Suh et al. |
| 2005/0149026 A1 | 7/2005 | Butler et al. |
| 2006/0116683 A1* | 6/2006 | Barrall ........... A61B 17/7059 606/71 |
| 2006/0200134 A1 | 9/2006 | Freid et al. |
| 2006/0235405 A1 | 10/2006 | Hawkes |
| 2006/0276794 A1 | 12/2006 | Stern |
| 2007/0213729 A1 | 9/2007 | Lindemann et al. |
| 2007/0270855 A1 | 11/2007 | Partin |
| 2007/0288010 A1 | 12/2007 | Alleyne |
| 2008/0065070 A1 | 3/2008 | Freid et al. |
| 2008/0097445 A1 | 4/2008 | Weinstein |
| 2008/0108998 A1 | 5/2008 | Lindemann |
| 2008/0114361 A1 | 5/2008 | Butler et al. |
| 2008/0154312 A1 | 6/2008 | Colleran |
| 2008/0177263 A1 | 7/2008 | Freedman et al. |
| 2008/0195100 A1 | 8/2008 | Capote et al. |
| 2008/0215097 A1 | 9/2008 | Ensign et al. |
| 2008/0234680 A1 | 9/2008 | Zaiser et al. |
| 2008/0243191 A1 | 10/2008 | Tipireni et al. |
| 2008/0269753 A1 | 10/2008 | Cannestra |
| 2009/0076509 A1 | 3/2009 | Bush, Jr. et al. |
| 2009/0082813 A1 | 3/2009 | Long et al. |
| 2009/0259226 A1 | 6/2009 | Michelson |
| 2009/0264934 A1 | 10/2009 | Youssef et al. |
| 2009/0275947 A1 | 11/2009 | Graham et al. |
| 2010/0114176 A1 | 1/2010 | Ibrahim et al. |
| 2010/0121329 A1 | 1/2010 | Ryan et al. |
| 2010/0063505 A1 | 3/2010 | Frigg et al. |
| 2010/0076495 A1 | 3/2010 | Lindemann |
| 2010/0082029 A1 | 4/2010 | Ibrahim et al. |
| 2010/0211108 A1 | 4/2010 | Lemole, Jr. |
| 2010/0234888 A1 | 4/2010 | McClintock et al. |
| 2010/0137909 A1 | 6/2010 | Osman |
| 2012/0083846 A1* | 4/2012 | Wallenstein ....... A61B 17/7059 606/279 |

* cited by examiner

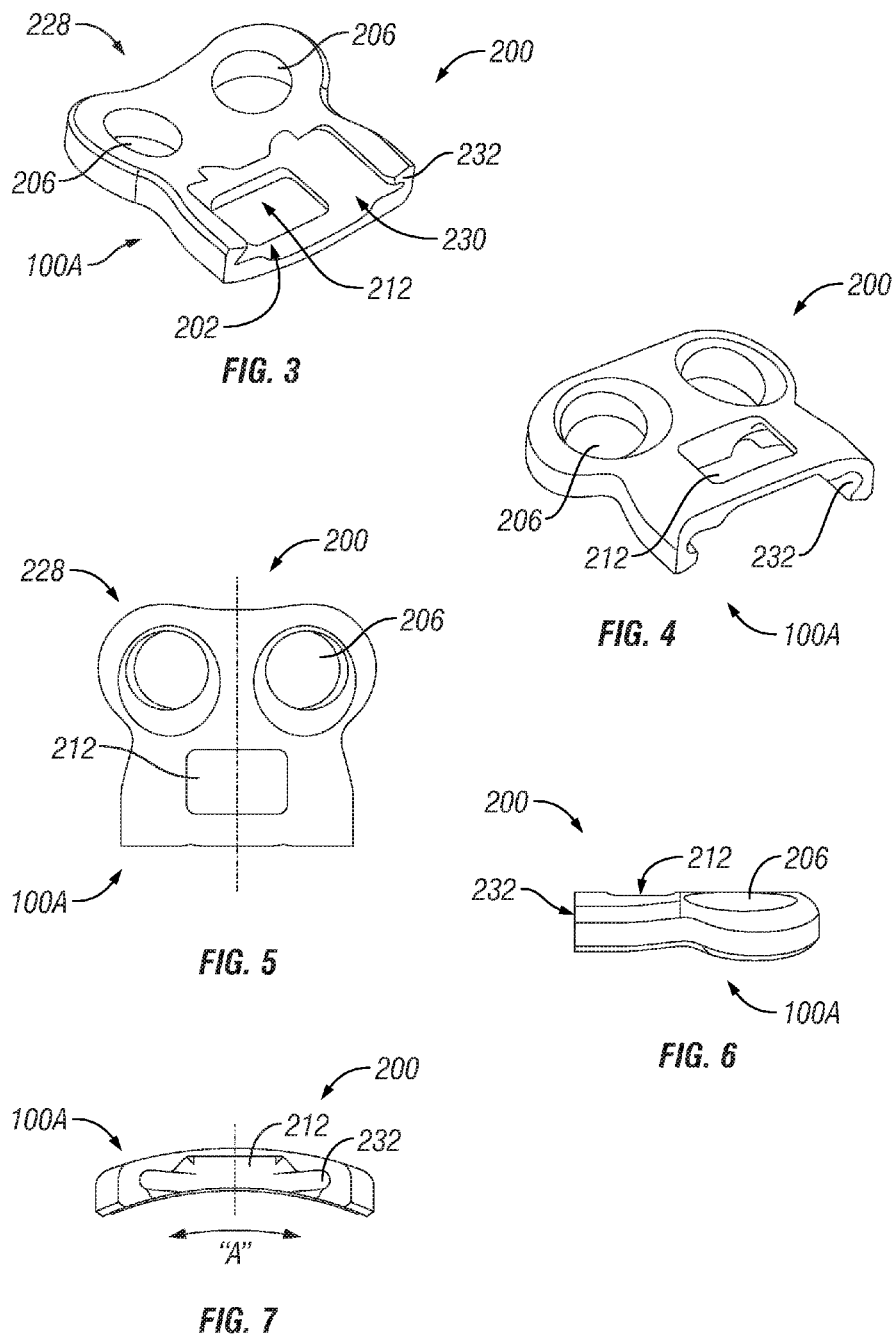

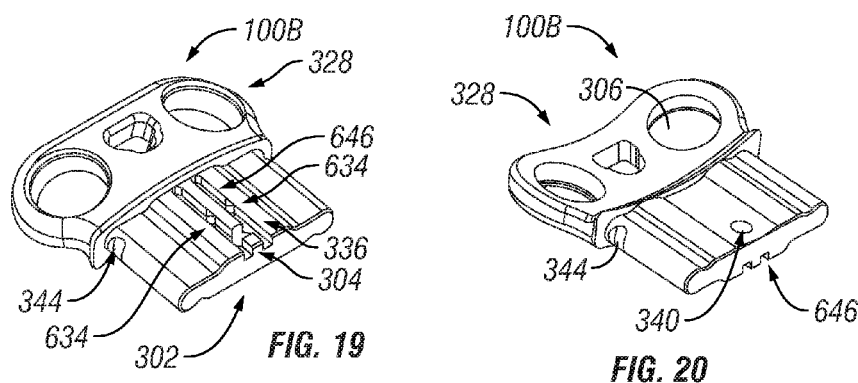
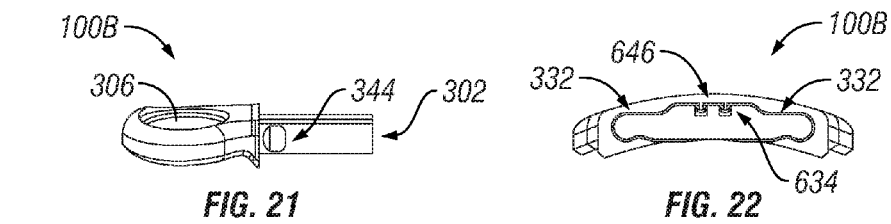
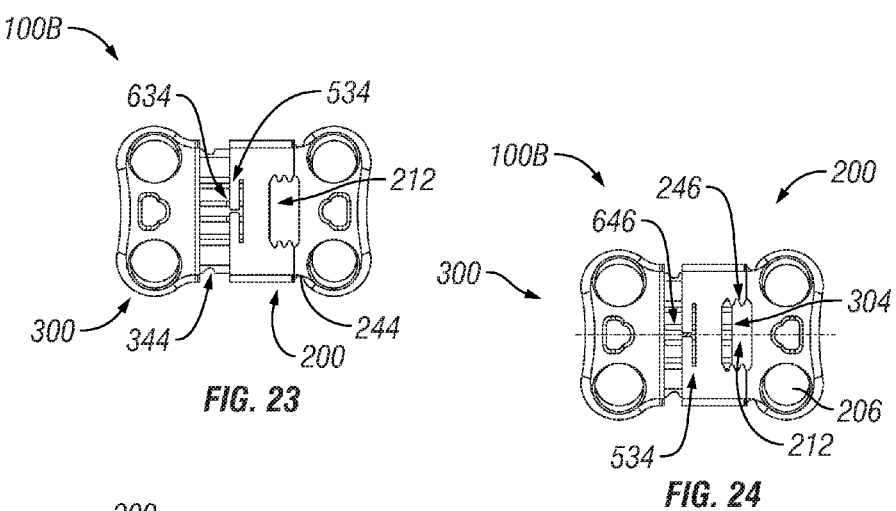
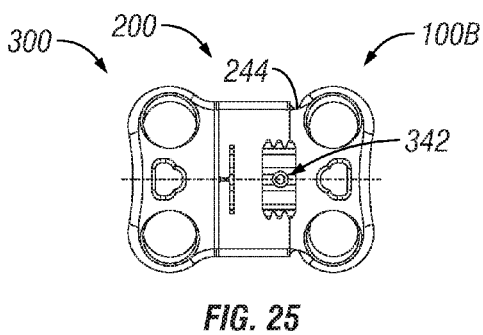

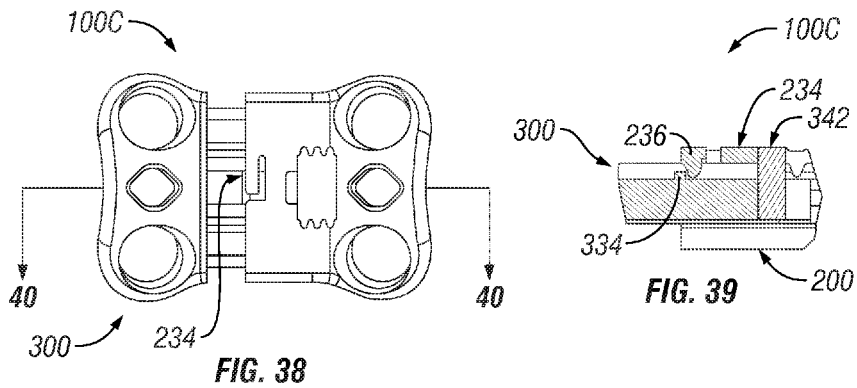
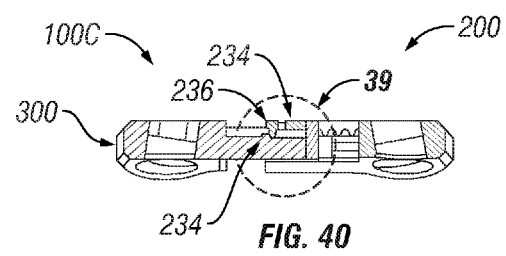
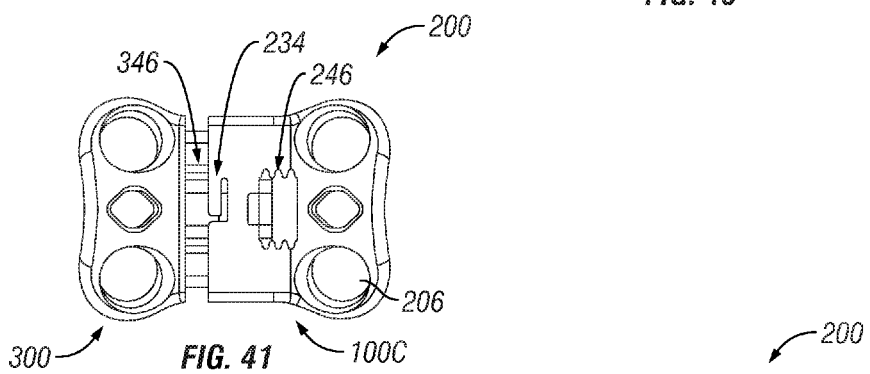
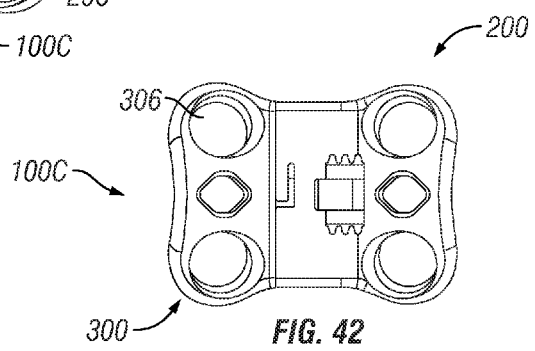

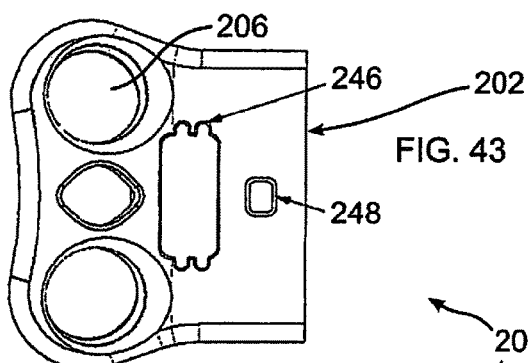
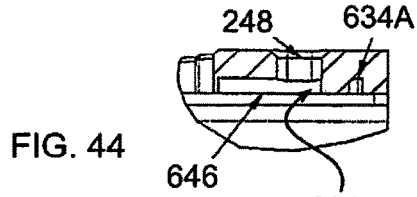
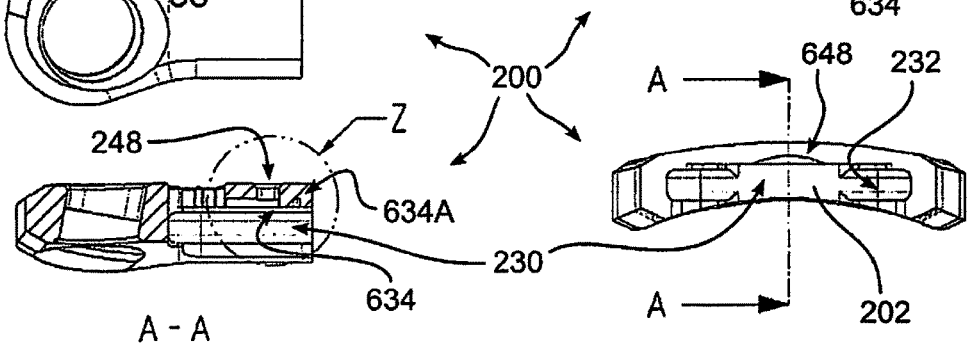
FIG. 43  FIG. 44
FIG. 45  FIG. 46
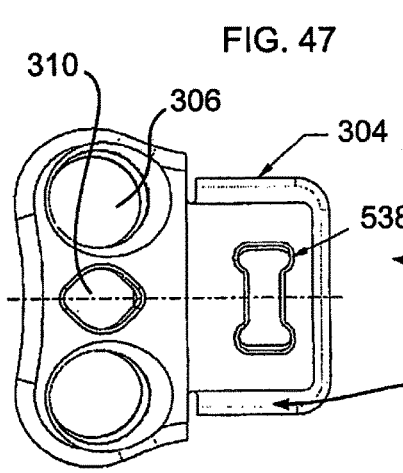
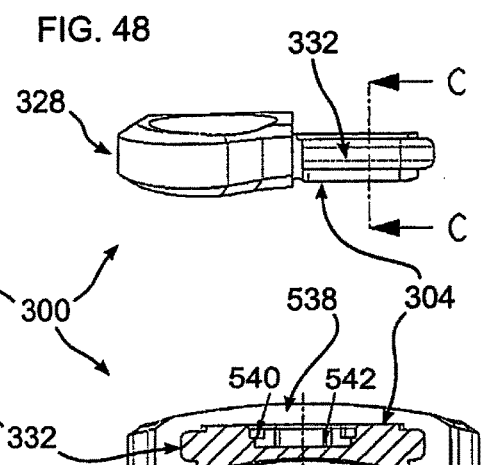
FIG. 47  FIG. 48
FIG. 49

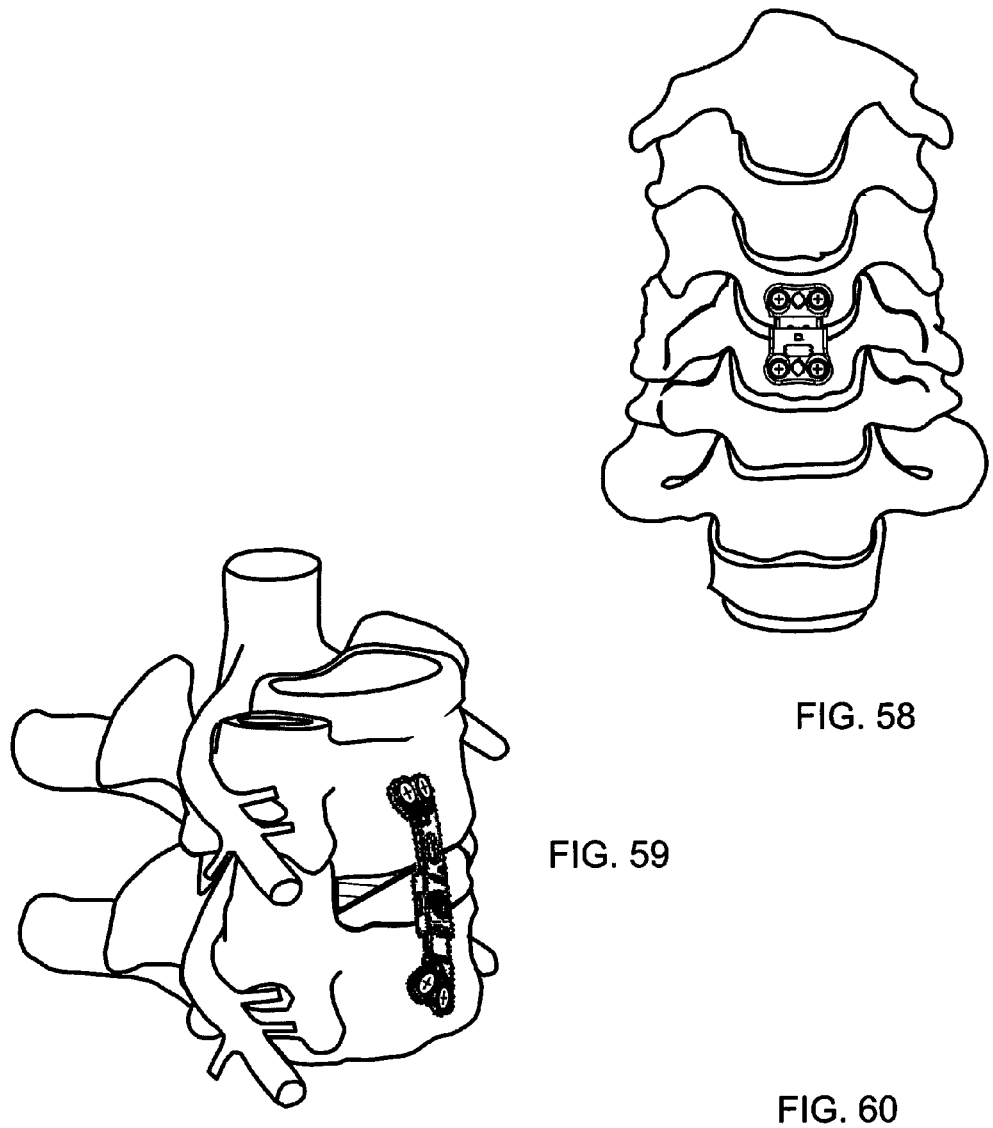
FIG. 58
FIG. 59
FIG. 60
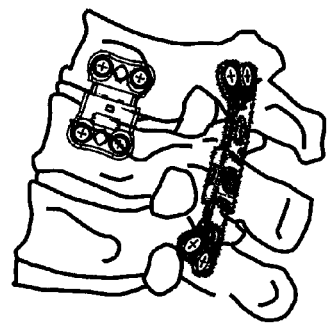

SPINE STABILIZATION

CROSS-REFERENCE TO RELATED APPLICATIONS

This application is a continuation application of U.S. patent application Ser. No. 14/749,897 filed Jun. 25, 2015 (published as U.S. Patent Publication No. 2015-0289909), which is a continuation application of U.S. patent application Ser. No. 13/086,122, filed Apr. 13, 2011 (now issued as U.S. Pat. No. 9,095,387), all of which are hereby incorporated by reference in their entirety.

FIELD OF THE INVENTION

The invention relates to bone fixation, and more particularly to fixation of spinal joints using compression imposed by mating plates.

BACKGROUND OF THE INVENTION

Spinal fusion, also known as spondylodesis or spondylosyndesis, is a surgical technique used to join two or more vertebrae. Supplementary bone tissue, from the patient (autograft), a donor (allograft), or from a synthetic material can be used in conjunction with the body's natural bone growth (osteoblastic) processes to fuse the vertebrae.

Wolfe's Law states that maintaining a compressive load on a graft in an interbody fusion contributes towards the graft fusing more quickly and or thoroughly.

SUMMARY OF THE INVENTION

An embodiment for stabilizing bones of a patient comprises a first plate portion including at least one aperture for connecting the first plate portion to body tissue of the patient comprises a projection extending from the first plate portion; a second plate portion including at least one aperture for connecting the second plate portion to body tissue of the patient; a chamber formed in the second plate portion sized and dimensioned to slidingly receive the projection, thereby substantially limiting movement of the first plate portion relative to the second plate portion to a telescoping motion when the projection is received within the chamber; a limiter resiliently extending from one of the projection or the chamber; a catch formed in the other of the projection or the chamber, relative to the limiter, operative to form an engagement with the limiter, the catch further operative to admit passage of the limiter past the engagement when the first and second plate portions are telescoped together, the catch further operative to prevent passage of the limiter past the engagement of the catch and the limiter when the first and second plate portions are telescoped apart.

In further embodiments, the projection forms at least two rails engageable with the chamber; the chamber forms at least two grooves mateable with the at least two rails; a groove formed in the projection or chamber forming the catch is positioned apart from a location of the engagement when the first and second plate portions are telescoped together, the groove operative to admit passage of the limiter between a first location at a first distance from the engagement and a second location disposed at a distance from the first location; an aperture is formed in the projection or chamber forming the catch, whereby an object may be inserted within the aperture to resiliently bend the limiter to disengage the limiter from the catch.

In yet further embodiments, an aperture is formed in the projection or chamber forming the catch, whereby an object may be inserted within the aperture to resiliently bend the limiter to disengage the limiter from the groove; and the limiter has a ramped surface and a blocking surface; the catch further includes a blocking surface, the blocking surface of the limiter mateably engageable with the blocking surface of the catch to prevent telescoping apart of the first plate portion and the second plate portion.

In another embodiment, the bones of the patient are jointed bones, and the first plate portion is engageable with bones of a first side of the joint, and the second plate portion is engageable with bones on a second, opposite side of the joint; when the first plate portion and the second plate portion are telescoped together, a compressive force is applied to the jointed bones; the compressive force is operative to promote a fusion of bones of the patient; the limiter forms a curved profile mateable with a curved profile of the catch; the chamber further includes a viewing aperture positioned formed in the chamber and operative to enable viewing of an extent of telescoping of the first plate portion with the second plate portion; and the viewing aperture includes formations enabling a quantification of an extent of telescoping of the first and second plate portions.

In yet another embodiment, a device for applying a compressive force to separated bones of a patient, comprises a first plate portion including at least one aperture for connecting the first plate portion to a first bone of the patient; a projection extending from the first plate portion; a second plate portion including at least one aperture for connecting the second plate portion to a second bone of the patient, the second bone separated from the first bone by a bone graft; a chamber formed in the second plate portion sized and dimensioned to slidingly receive the projection, thereby substantially limiting movement of the first plate portion relative to the second plate portion to a telescoping motion when the projection is received within the chamber; a catch formed in one of the projection or the chamber, operative to form an engagement with the limiter, the catch further operative to admit passage of the limiter past the engagement when the first and second plate portions are telescoped together, the catch further operative to prevent passage of the limiter past the engagement of the catch and the limiter when the first and second plate portions are telescoped apart; a limiter resiliently extending from the other of the projection or the chamber relative to the catch, and having a surface angled to slidingly engage the catch, and an opposing surface angled to resist movement when engaged with the catch; and a groove is formed in the projection or chamber forming the catch, the groove positioned apart from a location of the engagement when the first and second plate portions are telescoped together, the groove operative to admit passage of the limiter between a first location at a first distance from the engagement and a second location disposed at a substantial distance from the first location.

In another embodiment, a device for applying a compressive force to separated bones of a patient comprises a first plate portion including at least one aperture for connecting the first plate portion to a first bone of the patient; a projection extending from the first plate portion; a second plate portion including at least one aperture for connecting the second plate portion to a second bone of the patient, the second bone separated from the first bone by a bone graft; a chamber formed in the second plate portion sized and dimensioned to slidingly receive the projection, thereby substantially limiting movement of the first plate portion relative to the second plate portion to a telescoping motion when the projection is received within the chamber; a catch formed in one of the projection or the chamber, operative to form an engagement with the limiter, the catch further operative to admit passage of the limiter past the engagement when the first and second plate portions are telescoped together, the catch further operative to prevent passage of the limiter past the engagement of the catch and the limiter when the first and second plate portions are telescoped apart; a limiter resiliently extending from the other of the projection or the chamber relative to the catch, and having a surface angled to slidingly engage the catch, and an opposing surface angled to resist movement when engaged with the catch; and a viewing aperture positioned in the chamber and operative to enable viewing of an extent of telescoping of the first plate portion with the second plate portion.

In a yet further embodiment, the limiter includes a relief formed in the projection or chamber from which the limiter extends, the limiter operative to resiliently bend and deflect into the relief.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 3 through 14 depict various views of a second embodiment of mateable stabilization plates;

FIGS. 15-22 depict various views of a third embodiment of mateable stabilization plates, including limiters;

FIGS. 23-25 depict the embodiment of FIGS. 15-22, in three different states of compression;

FIGS. 30-42 depict various views of a fourth embodiment of mateable stabilization plates;

FIGS. 43-57 depict various views of a fifth embodiment of mateable stabilization plates, including a resilient and separable limiter; and FIGS. 58-60 depict alternative examples of implantation of embodiments of mateable stabilization plates.

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein are not to be considered as limiting of the present invention.

Figure 1:
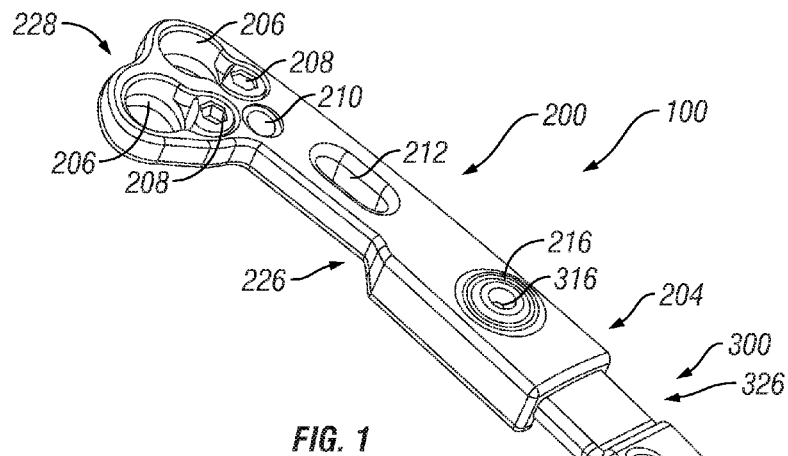
FIGS. 1 and 2 depict perspective views of a first embodiment of mateable stabilization plates.
Figure 2:
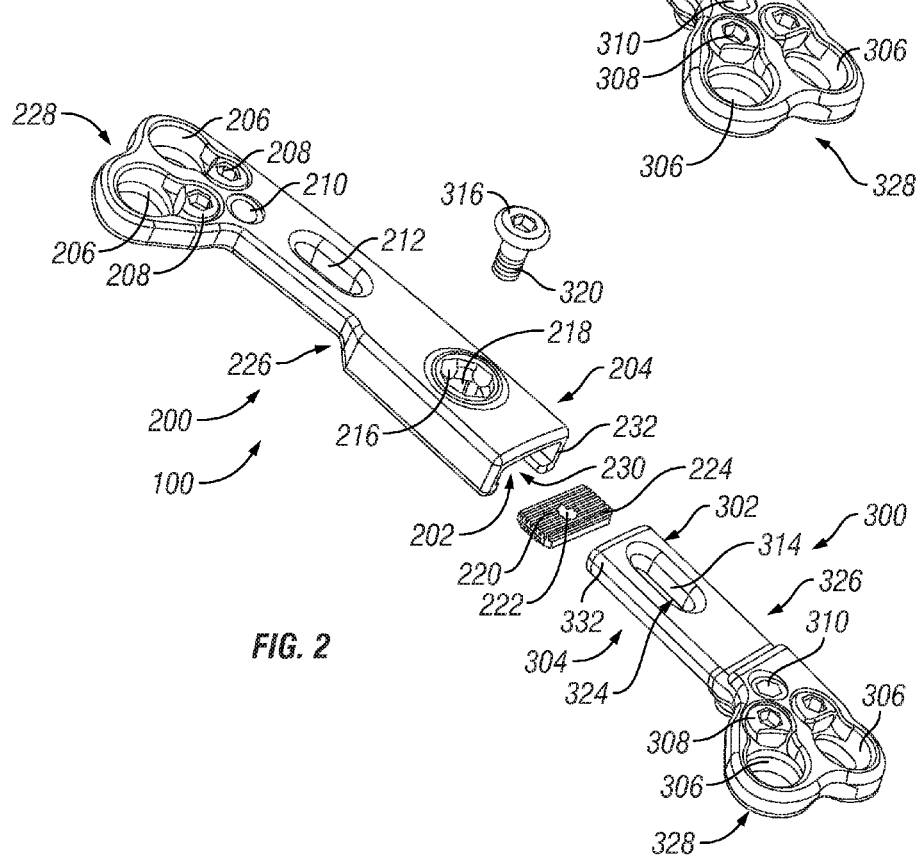
Figure 8:
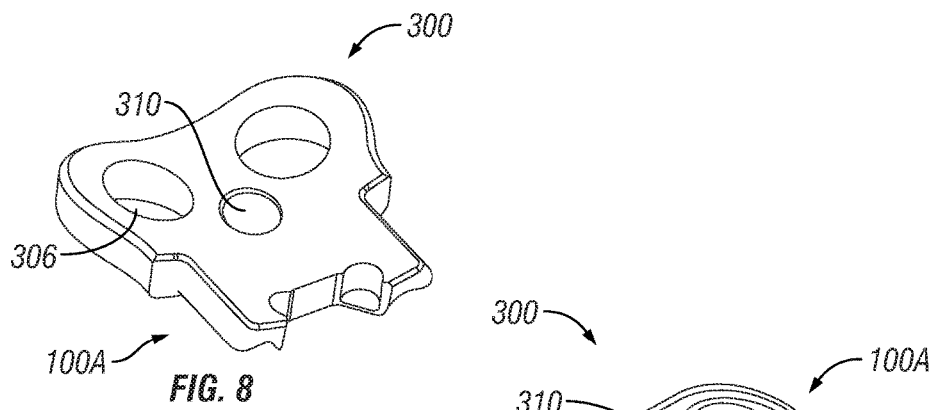
Figure 9:
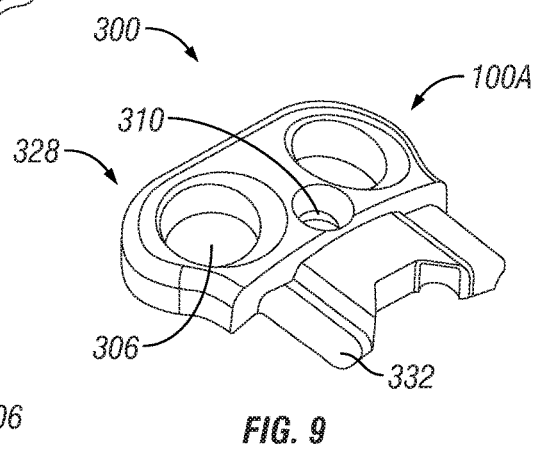
Figure 10:
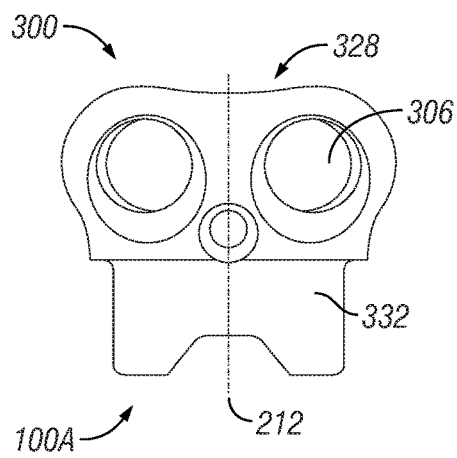
Figure 11:
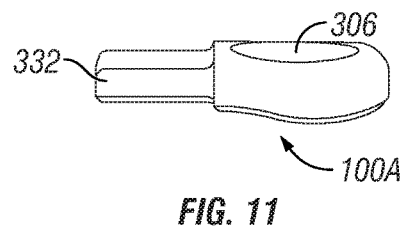
Figure 12:
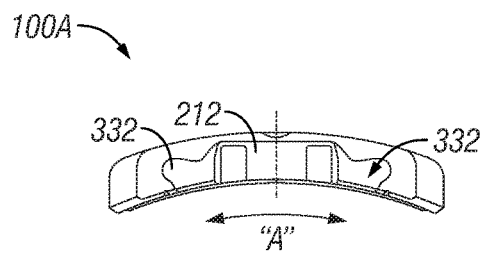

Referring now to the figures, in which like reference numerals refer to like elements, FIGS. 1-2 illustrate a bone stabilization device 100 including a receiver 200 and an insert 300. A chamber 202 open at an end 204 of section 200 is sized and dimensioned to slidably receive and retain a projection 302 disposed at an end 304 of insert 300. Receiver 200 and insert 300 are provided with one or more fastener apertures 206, 306, respectively, operative to facilitate connection of receiver 200 and insert 300 to bones or other tissue of a patient.

With reference to FIGS. 58-60, it may be seen that device 100 is implantable within the body, in connection with vertebrae 502, 504, 506 of the spine 500. The vertebrae shown are exemplary, and devices disclosed herein may be used with any vertebrae of the spine. Device 100 may be connected to an anterior, posterior, medial, or lateral aspect of the spine, using any acceptable approach, or any known method, including open or minimally invasive. Device 100 may further be connected anteriorly, posteriorly, or laterally, to non-adjacent vertebrae, as may be seen for example in FIG. 59. While device 100 is advantageously used to stabilize vertebrae, other bones of the body may be stabilized using device 100, including other joints, or to stabilize non-jointed portions of bones, for example bones that have been fractured.

With further reference to FIGS. 1-2, locking elements 208, 308 may be provided, operative to ensure fasteners inserted within apertures 206, 306 do not reverse from engagement with the body.

Additional apertures 210, 212, 310, 312 may be provided to operatively serve at least one of the following: engaging fasteners, provide an observation window to underlying areas, provide an access port to underlying tissue, provide an area to pack bone graft or other bone growth stimulating materials and/or releasably connect device 100 with surgical or manipulative instrumentation. Elongated aperture 314, visible in FIG. 2, slideably receives a fastener 316 which is passed through an opening 216 in chamber 202. Locking means 218 may be provided to ensure fastener 316 remains in secure engagement with device 100, including, for example, knurling, a locking washer, a cover, or a lock engageable with a portion of fastener 316, such as is shown, for example, as lock 208. Insert 300 may further be secured relative to receiver 200 at any point along the length of aperture 314 in which post 320 may reside, whereby a continuous range of adjustment is possible.

It may be desired to allow receiver 200 and insert 300 to remain in mutual slideable engagement within the body. Therapeutic benefits would include restricting ranges of motion, for example flexion or extension, while enabling compression and distraction. In this application, it may be advantageous for fastener 316 to securely engage a portion 202, as by threading, compression, adhesion, or welding, whereby a post portion 320 of fastener 316 may freely slide within aperture 314 of insert 300. Alternatively, not shown, chamber 202 may be provided with an elongated aperture as shown for aperture 314, and a post 320 may be associated with insert 302.

In another application, it may be advantageous to fasten receiver 200 and or insert 300 to the body, therapeutically adjust a disposition of bones of the body, and then securely fasten receiver 200 and insert 300 in a fixed relative configuration. In this application, it may be advantageous to connect receiver 200 and insert 300 in slideable alignment, and expeditiously tighten receiver 200 and insert 200 together once a desired position has been attained. Accordingly, connector 220 may releasably engage fastener 316, for example by threaded attachment 222, whereby when post 320 passes through opening 216, through aperture 314, and into engagement with connector 220, receiver 200 and insert 300 may slide relative to each other, but not separate. When a disposition of bones has been achieved, fastener 316 may be securely fastened to connector 220, whereupon projection 302 is pinched against one or more surfaces of chamber 202, and may no longer slide relative to chamber 202. To promote a secure connection between projection 302 and chamber 202, a surface 224 of connector 220 may be provided with a knurled or roughened surface, as may a complementary contacting surface 324 of projection 302 and or chamber 202. For additional strength or reliability, a plurality of fasteners 316 and or connectors 220 may be used. A single fastener has an advantage of quick installation and adjustment, decreasing the duration of surgery.

Receiver 200 and insert 300 may advantageously be assembled and sterilized prior to surgery, together with fastener 316 and connector 220, for example as part of a manufacturing and quality control process, thereby facilitating surgical preparation by eliminating interoperative assembly, and reducing the complexity and duration of surgery, while reducing the probability of assembly error.

In yet another application, receiver 200 and insert 300 are mutually connected, and engaged to respective portions of body tissue. Subsequently, receiver 200 and insert 300 are each engaged by an instrument, not shown, for example through connection with one or more of aperture 310 of insert 300, and aperture 210, 212, or narrowed portion 226, of receiver 200. In this manner, receiver 200 and insert 300 may be compressed together, or expanded apart, thereby producing a commensurate change in the relative alignment of attached tissue, whereupon fastener 316 may then be tightened to maintain a desired alignment. A slot 230 may be provided, formed in a portion of chamber 202, operative to admit passage of a portion of fastener 316, to permit passage of body fluids or tissue ingrowth into chamber 202, to reduce weight of device 100, and or to facilitate attachment of connector 220.

Receiver 200 and insert 300 interconnect in sliding mutual engagement along a predetermined pathway which may be straight or curved, defined by mating rails 332 and grooves 232, each of rail 332 guided along a pathway defined by a respective groove 232. In this manner, telescoping movement of receiver 200 and insert 300 may be defined to a single plane or curved pathway, thereby enabling compression or distraction, while stabilizing along other axes. The mating rail 332 and groove 232 enable a bending or twisting load to be distributed across the length of mutual engagement of rails 332 and grooves 232, providing increased strength, reducing the incidence and severity of potential stress raisers, and preventing disengagement along an anterior-posterior direction when device 100 is implanted in the spine.

Receiver 200 and insert 300 are each provided with a narrowed portion 226, 326, respectively, advantageously sized to facilitate insertion of device 100 into the body through a percutaneous puncture or minimal incision, to provide good visualization of underlying tissues, and or to reduce impact upon surrounding tissues at the site of implantation. Further, head portions 228, 328 may be angled, and or provided with curved surfaces, to better conform to intended attachment surfaces in the body. As such, device 100 may be provided in left or right configurations, and may be provided in a range of sizes or configurations appropriate for the size, gender, or age of the patient. For each size, device 100 enables a low profile, or reduced dimensional size, thereby reducing dislocation of body tissue, facilitating implantation, and increasing patient comfort.

As a sliding or telescoping engagement is formed between receiver 200 and insert 300 at a location disposed away from bone engaging head portions 228, 328, greater flexibility in an orientation and shape of head portions 228, 328 is possible. In particular, portions of device 100 that interface with the spine may be contoured to match the natural anatomy of the vertebral bodies, without a requirement of slots or adjustments at these interface regions. Accordingly, an optimal configuration, for example, of apertures 206, 306 and associated locking mechanisms 208, 308, is achieved.

Device 100 may be used, for example, in the case of a trauma, tumor or deformity in the human spine where one or more vertebral bodies are compromised. In certain instances, it is advantageous to perform a corpectomy where the damaged portions of the vertebrae are removed. A cage or bone graft is inserted into the resulting space to replace the removed tissue. In addition to the cage or graft, device 100 is provided operative to span the now weakened area, and provide stabilization while tissues reform and native strength is restored, or as a longer term source of stabilization.

In an application, a compressive force is applied by device 100 to a bone graft or other implanted material, and or bones or other tissue of the patient, whereby Wolfe's Law may apply. After an initial implantation, an increase or decrease in compressive force may be achieved by loosening fastener 316, changing a disposition of body tissue, and refastening 316, for example through a minimally invasive procedure. Such increase in compressive force may advantageously compensate, for example, for graft subsidence.

Referring now to FIGS. 3-12, an alternative device 100A includes grooves 232 and rails 332 which mutually form a tongue and groove connection. In this embodiment, receiver 200 and insert 300 are provided with a curved profile indicated by arrow "A", which is operative to conform to curved anatomy at an implant location, and or to provide additional bending stiffness for device 100A, for example to reduce a likelihood of bending in a direction transverse to curve "A", corresponding to flexion and extension of the spine. In another embodiment, receiver 200 and insert 300 may also be provided with a curved profile extending in a transverse direction from arrow "A." In addition, grooves 232 and rails 332 are angled with respect to the coronal plane of the spine, providing additional resistance to bending of device 100 when implanted in an AP orientation. Further, by disposing rails 332 at an angle, an increased quantity of material may be used to form rails 332, manifested in an enlarged cross-section of the jointed surfaces, thereby increasing the strength of the mated receiver 200 and insert 300. Further, the angled disposition exhibits a tendency for self-centering, and is thereby less prone to a toggling or side to side movement, thereby transmitting load more evenly throughout the mated rail 332 and guide 232 surfaces, resulting in an increased strength and durability. More particularly, a position of lowest potential energy exists in which rails 332 and grooves 232 are lying at the same angle with respect to each other, due to their mutually ramped angular disposition relative to a direction of sliding engagement.

Figure 13:
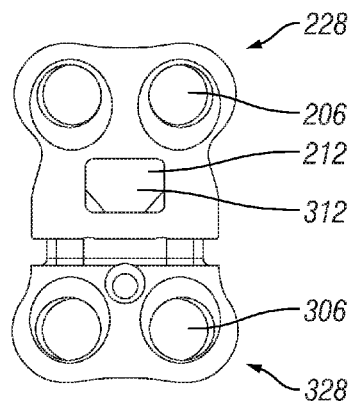
Figure 14:
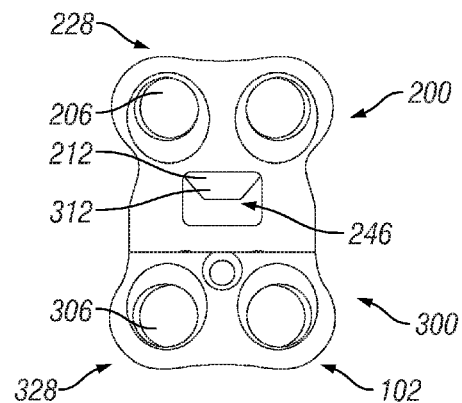
Figure 15:
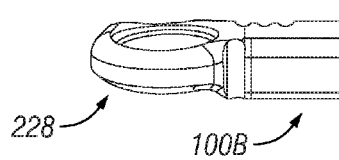

Device 100A is illustrated in FIGS. 13-14, with rails 332 inserted within grooves 232, with FIG. 14 illustrating a complete extent of compression. With reference to overlapping apertures 212, 312, a visible indication of an extent of compression may be seen, by direct observation in the assembly or operating theatre, and with imaging, which may be facilitated if device 100A is formed with radiopaque material at least in this area.

Devices of the various embodiments disclosed herein enable a reduction or elimination of movement of a stabilizing plate relative to a bone screw or anchor head, thereby reducing disease caused by an implant element rubbing or contacting body tissue, including an adjacent disc.

With reference to FIGS. 15-29, an alternative embodiment, device 100B, is illustrated, which forms a hybrid stabilizer having a dynamic range of compression following an initial amount of static compression. Device 100B includes one or more limiters 534 engageable with one or more catches 634. Limiter 534 includes a projecting surface 536 resiliently connected to receiver 200. In the embodiment of FIGS. 15-29, extension 238 resiliently depends from receiver 200, and projecting surface 536 is disposed about an end of extension 238.

Where two or more limiters 534 are used, it is advantageous to ensure all limiters are engaged to their respective catches 634 at the same time. With appropriate design and manufacturing tolerances, the sliding coordination of rails 332 and grooves 232 reduces side to side, jamming, or toggling motions of receiver 200 and insert 300, which could otherwise enable an uneven engagement.

Projecting surface 536 is advantageously formed with a steeply angled surface 550 extending in a direction away from head portion 228, and a ramped surface extending in direction towards head portion 228. In this manner, when receiver 200 and insert 300 are assembled together, projecting surface may be deflected by catch 634 to resiliently bend extension 238 to admit passage of limiter 534 past catch 634. Similarly, the steeply angled surface of projecting surface 536 is thereafter constrained against a mating surface of catch 634 whereby extension 238 is not caused to bend, and maintenance of a mutual engagement of receiver 200 and insert 300 is thus fostered. A force required to bend extension 238 may be targeted to result in resistance to engagement of limiter 534 and catch 634 until a sufficient compressive force is applied to the receiver 200 and insert 300. In this manner, a device implanted with an unengaged limiter 534 may become engaged when a sufficient range of motion has been achieved, for example during therapeutic exercise, or after a predetermined extent of graft subsidence or tissue healing has occurred.

Figure 16:
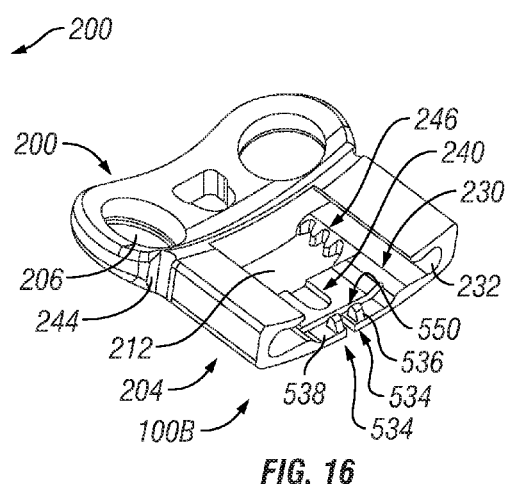
Figure 17:
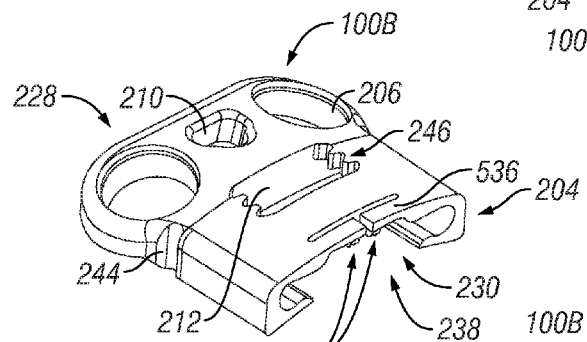
Figure 18:
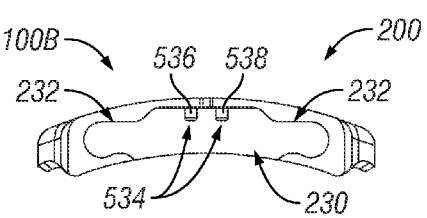
Figure 26:
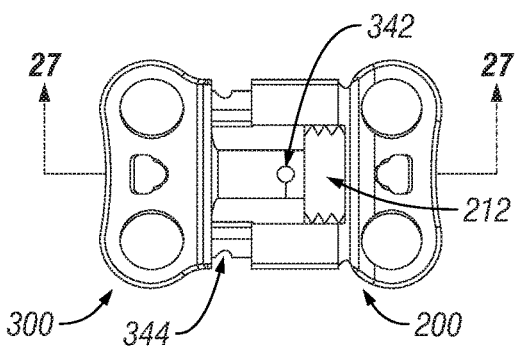
FIGS. 26-29 depict alternative views of the embodiment of FIGS. 15-25.
Figure 27:
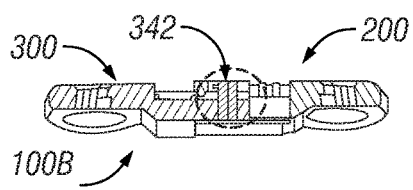
Figure 28:
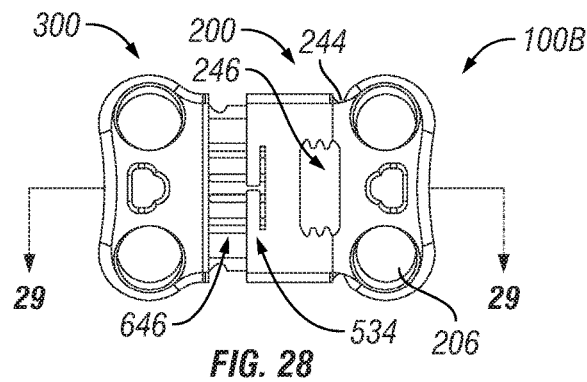
Figure 29:
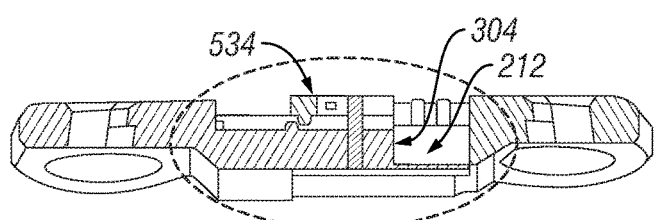
Figure 30:
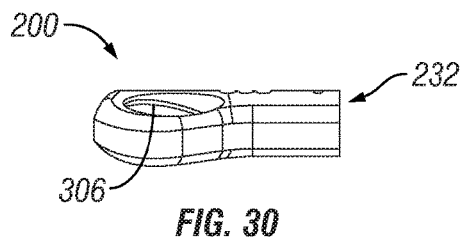
Figure 31:
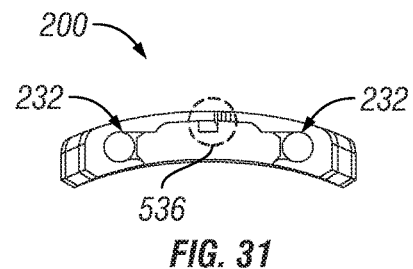
Figure 32:
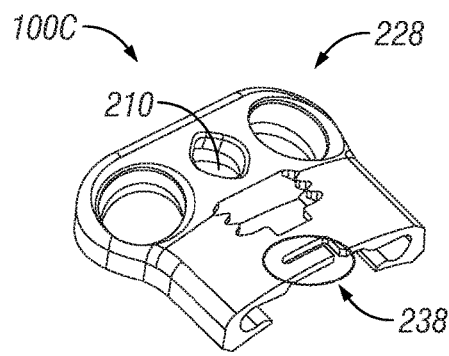
Figure 33:
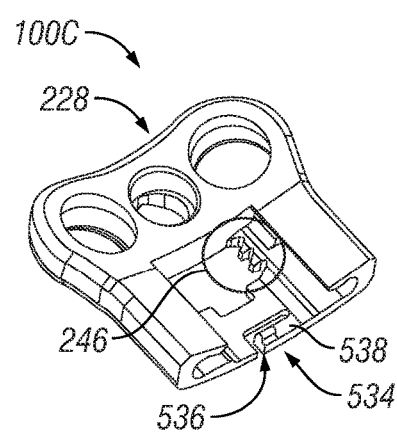
Figure 34:
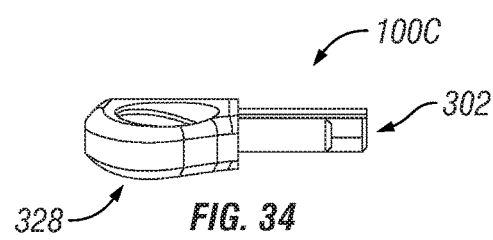
Figure 35:
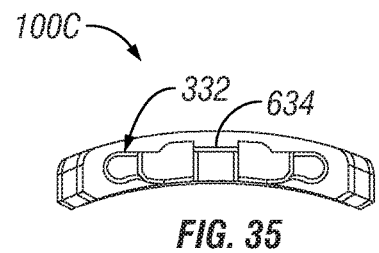
Figure 36:
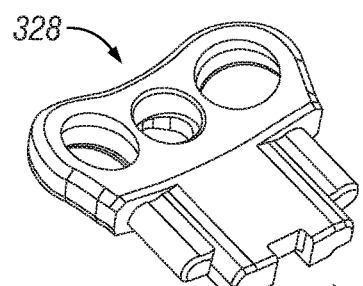
Figure 37:
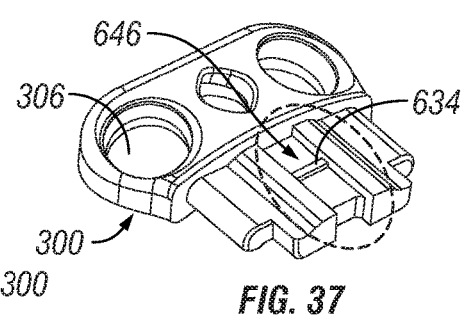

A groove or channel 240 may be seen in FIG. 16, having a purpose best understood with further reference to FIGS. 19-20, and 27-29, in particular. An opening 340 is provided in insert 300, operative to admit passage of a pin 342 through end 304 and into channel 240, when insert 300 is assembled into receiver 200. Access to end 304 of insert 300, for insertion of pin 342 after assembly, is provided through slot 230 of receiver 200. When pin 342 is disposed through insert 300 and within channel 240, movement of receiver 200 and insert 300 relative to each other is constrained to an extent of travel of pin 342 within channel 240. As such, receiver 200 and insert 300 are further maintained in an interconnected state by pin 342. It may be advantageous to preassemble receiver 200 and insert 300 as part of a manufacturing process, or prior to surgery. In this manner, for example, pin 342 is assembled into end 304 and channel 240; however, receiver 200 and insert 300 are advantageously not sufficiently collapsed together to a point where limiter 534 is engaged past catch 634.

In the operating theatre, receiver 200 is engaged with body tissue, for example a first vertebra, and insert 300, preassembled into receiver 200 and optionally retained therein by pin 342, is engaged with a different portion of body tissue, for example a second vertebra. Engagement of receiver 200 and insert 300 is by any known means, including screws, polyaxial screws, pedicle screws, bone screws, staples, clips, anchors, adhesive, suture, and or wire. Advantageously, graft material is placed into the body prior to engagement of device 100B.

Once receiver 200 and insert 300 are engaged with the body, tissue and or graft material positioned between engaged body portions may be compressed towards each other. In one embodiment, the body tissue is compressed using any known means, including directly engaging the body tissue. In another embodiment, receiver 200 and insert 300 are directly manipulated and moved closer together into further mutual sliding engagement, and through their respective connections with body tissue, cause the body tissue portions to move or to be compressed together. To facilitate this action, one or more engagement formations 244 in receiver 200, and or engagement formations 344 in insert 300, are operative to enable secure engagement with a compression instrument, not shown. Such compression instrument may be of a prior art design, for which device 100B is adapted, or an instrument may be adapted or created for engagement with specific engagement formations 244, 344 of device 100A. Engagement formations 244, 344 may have the form, for example, of depressions, projections, or apertures, and may be threaded or otherwise configured for secure engagement with a hand, and or an instrument or tool.

It is contemplated that an initial amount of compression engages limiter 534 and catch 634, whereby the body tissue portions may further compress, however a minimum amount of compression is continuously maintained, advantageously sufficient to exploit Wolfe's Law. Limiter grooves 646 may be provided to protect and guide limiters 534 during relative movement of receiver 200 and insert 300.

Aperture 212 is provided with indicating formations 246, spaced at regular intervals, for example 1 mm, although other intervals may advantageously be employed. Indicating formations may have the shape of a projection extending into aperture 212, or may be formed as one or more angled lines, as may be seen in FIGS. 13-14. Through direct observation through aperture 212, inter-operatively and or through imaging, an alignment of a surface of insert 300 with respect to indicating formations 246 serves to indicate an extent of compression of receiver 200 relative to insert 300. Knowledge of an extent of compression may be used to understand a current disposition of body tissue, and to plan and measure a therapeutic change in compression.

Referring now to FIGS. 23-25, the aforedescribed levels of compression of device 100B may be seen. In FIG. 23, limiters 534 have not engaged, or passed beyond, catches 634, and no portion of insert 300 is visible within aperture 212, indicating a current state of assembly. Although not required, pin 342 has advantageously been engaged within channel 240. In FIG. 24, limiters 534 have passed beyond catches 634, and if device 100B were implanted, a minimum amount of compression would be achieved. End 304 of insert 300 is now visible within aperture 212. In particular, a line demarcating end 304 may be compared with indicating formations 246. For example, indicating formations 246 may be positioned 1 mm apart, or any other distance apart which may be meaningful for a particular therapeutic application. It may be seen that if a distance between indicating formations 246 is known, an extent of compression may be determined. In FIG. 25, receiver 200 and insert 300 are fully compressed; however, it should be noted that movement apart of receiver 200 and insert 300 is possible.

It may be advantageous to impose an initial amount of compression not only to encourage tissue growth, ingrowth, or fusion. An objective of a medical practitioner may be to insert an amount of graft or implant material sufficient to cause a desired amount of compression between body tissue and the implanted material, whereby surrounding body tissue, for example ligamentous tissue, provides the compressive force. However, if excess tissue is removed, or surrounding tissue does not create sufficient compression, the initial force imposed by engaging limiter 534 and catch 634 may provide the requisite compression. In addition, further compression may be imposed during flexion and extension of the joint. For example, receiver 200 and insert 300 may freely move further together due to natural kinematics of the joint.

While limiter 534 is shown and described as connected to receiver 200, it should be understood that catch 634 may be connected to receiver 200, and limiter 534 may be connected to insert 300. It is further noted that rails 332 and mating grooves 232 of device 100B are shaped with a different angle than corresponding rails 332 and grooves 232 of device 100A, although it should be understood that rails 332 and grooves 232 of device 100B may have the same or similar angle to that of device 100A.

Similarly, other features and corresponding advantages of the various embodiments herein may be interchanged or combined, as would be understood by one skilled in the art. More particularly, each embodiment of device 100 illustrates a particular combination of features, and for clarity, not all features or combination of features are illustrated for each device.

With reference to FIGS. 30-37, device 100C illustrates an alternative embodiment having a single limiter 534 and single catch 634. As with device 100B, extension 238 is dimensioned and configured to flex and admit passage of projecting surface 536 over catch 634 when insert 300 is urged towards receiver 200 with a predetermined minimum force. In one embodiment, this minimum force corresponds to correct implantation by the medical practitioner, whereupon engagement of projecting surface 536 and catch 634 will introduce a proper compressive force to promote Wolfe's Law. In another embodiment, this minimum force corresponds to a postoperative range of motion indicating that a minimum compressive force should be established and thereafter maintained.

Devices of the disclosure advantageously adjust for changes in graft height, postoperatively, as needed. In this manner, load may be maintained on graft of an interbody fusion to ensure that the graft is fused thoroughly and as quickly as possible, in accordance with Wolfe's Law. For cervical plating, in particular, a semi-rigid fixation may be advantageous. Devices of the disclosure accommodate this requirement by enabling a height adjustment postoperatively. This adjustability is provided by segments, or insert 300 and receiver 200, that telescope, or collapse and or expand in mutual connection, to a therapeutically effective height, thereby ensuring graft contact with the vertebral body endplates. By combining this dynamic aspect with a limiter 534, the amount of unloading of the graft may be limited, while preserving a dynamic height adjustment. Limiter 534 thus has at least two functions: helping to maintain receiver 200 and insert 300 in telescoping engagement, and providing a minimum amount of compression.

Reference may now be had to FIGS. 43-57, illustrating device 100D. In FIGS. 43-46 in particular, receiver 200 is illustrated in which limiter 534 is positioned to extend from insert 300, and catch 634 and limiter groove 646 are positioned within receiver 200. An additional catch 634A is positioned to engage limiter 534 prior to engagement of limiter 534 with catch 646, as explained further below.

Figure 50:
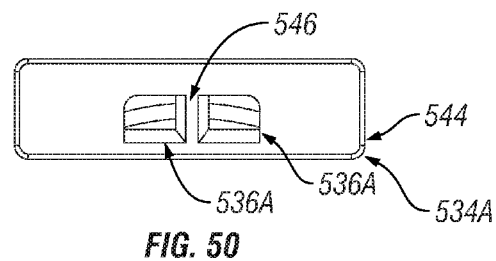
Figure 51:
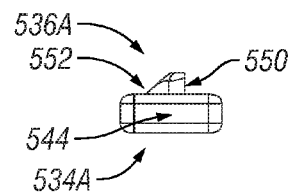
Figure 52:
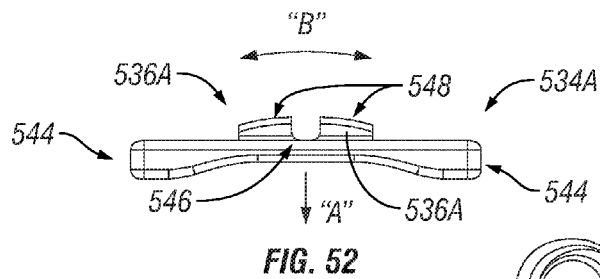
Figure 54:
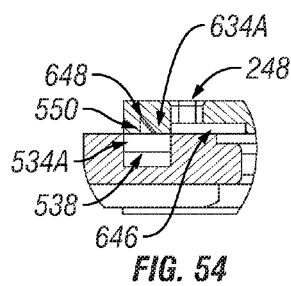
Figure 53:
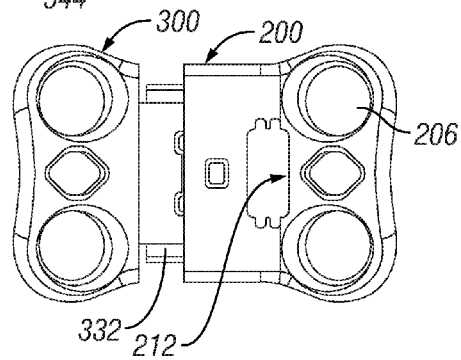
Figure 55:
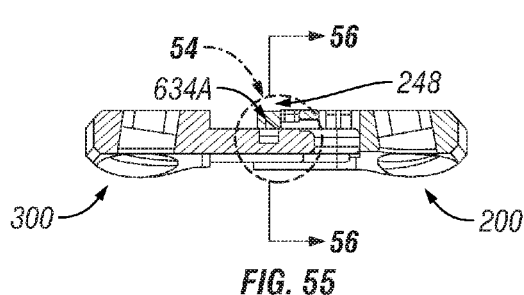
Figure 56:
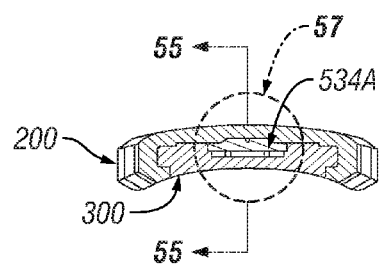
Figure 57:
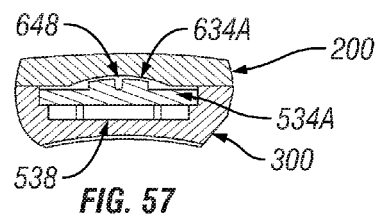

In FIGS. 47-49, insert 300 includes a chamber or spring relief 538 positioned within end 304, illustrated in cross section in FIG. 49. Notched steps 540 are formed at opposite ends of relief 538. A relief floor 542 is positioned at a greater depth within relief 538 than steps 540. With reference to FIGS. 50-52, a limiter 534A includes a projecting surface 536A. Limiter 534A is illustrated as a separate element relative to insert 300, although it should be understood that limiter 534A may be connected to insert 300, for example with a living hinge (not shown) at an end 544 of insert 300. However, it may be simpler, for example, to manufacturing limiter 534A separated, as shown. Opposing ends 544 of limiter 534A rest upon steps 540 of relief 538, whereby limiter 534A may resiliently bend downwards in a direction indicated by arrow "A". Hinge 546 is formed as a notch between projecting surfaces 536A, enabling projecting surfaces 536A to move closer together during bending of limiter 534A at hinge 546.

A curved profile, indicated by arrow "B", is formed by upper surfaces 548 of projections 536A. This curved profile corresponds to that of arch 648 of receiver 200, shown in FIG. 46. As insert 300 is moved into receiver 200, upper surfaces 548 mate with arch 648, together uniformly distributing a load or force of deflection to smoothly and reliably guide projections 536A downwards, thereby deflecting limiter 534A at hinge 546, in the direction of arrow "A". Relief 538 is sized and dimensioned so that limiter 534A may only resiliently deflect towards relief floor 542, and limiter 534A is prevented from movement in other directions.

As insert 300 of device 100D is passed into receiver 300, engaging rails 332 and grooves 232, an initial catch 634A mates with projecting surfaces 536A, after which insert 300 and receiver are retained in mutual engagement by an engagement of steeply angled surface 550 and a mating surface of initial catch 634A. Engagement at this level may be used, for example, to maintain insert 300 and receiver 200 in mutual engagement, or to impose a minimum level of compression of body tissue as described elsewhere herein. Insert 300 may be urged further within receiver 200, as by use of a compression tool during surgery, or through carrying out sufficient range of motion of body tissue connected to device 100D. Movement of insert 300 further into receiver 200 causes projecting surfaces 634A to deflect limiter 534A, bending hinge 546, through interaction of ramped surface 552 (FIG. 51) of projecting surfaces 536A against arch 648. After insert 300 has moved a sufficient distance, projecting surfaces 536A abut limiter groove 646, allowing limiter 534A to resiliently resume an unbent configuration, wherein limiter 534A now limits movement of insert 300 to an extent of a length of limiter groove 646. As with initial catch 634A, limiter groove 646 forms a mating surface with steeply angled surface 550, whereby insert 300 is maintained within receiver 200. To disengage limiter 634A from engagement within limiter groove 646, an object, such as a tool, may be inserted within opening 248, to deflect limiter 634A and clear steeply projecting surface s 636A from engagement within limiter groove 646. A similar opening, not shown, may be provided to enable disengagement from initial catch 634A.

In one embodiment, by first engaging initial catch 634A, an initial or minimum compression is applied to a bone graft. This minimum compression is maintained, while a dynamic range of motion imposing at least this minimum compression may subsequently be enabled by device 100D, when limiter groove 646 is engaged. Subsequent to enabling the dynamic range of motion, an excess unloading of the graft is ensured through engagement at a limit of limiter groove 646. In this manner, levels of tensile or extension movement are established which foster healing in accordance with Wolfe's Law.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A surgical system comprising:
an intervertebral device; and
a compression device, wherein the compression device comprises:
a receiver member, the receiver member including a limiter; and
an insert member configured to be received in the receiver member, the insert member including a catch configured to engage the limiter,
wherein the insert member comprises an opening configured to receive a pin,
wherein the receiver comprises a channel configured to engage the pin, and
wherein the pin is configured to travel within the channel to constrain movement of the receiver member relative to the insert member prior to the catch engaging the limiter so that receiver and insert remain in an interconnected state, and
wherein the compression member is configured to allow a dynamic range of compression such that the length of the compression member can increase or decrease following an initial amount of static compression.

2. The system of claim 1, wherein the compression device is capable of changing from a first length to a second length following compression of the device.

3. The system of claim 1, wherein the receiver member includes one or more apertures to receive fasteners and the insert member includes one or more apertures to receive fasteners.

4. The system of claim 3, wherein the receiver member includes two or more limiters and the insert member includes two or more catches, each catch configured to engage an associated limiter.

5. The system of claim 1, wherein the receiver member includes one or more grooves that engage one or more rails of the insert member.

6. The system of claim 5, wherein the one or more grooves and the one or more rails are slidably connected and configured to ensure proper engagement between the receiver member and the insert member.

7. The system of claim 1, wherein the limiter contains a projecting surface.

8. The system of claim 7, wherein the projecting surface is resiliently connected to the receiver member.

9. The system of claim 1, wherein the system further comprises graft material that is packed into the intervertebral device.

10. A surgical system comprising:
an intervertebral device configured to be inserted into a space between adjacent vertebrae; and
a compression device, wherein the compression device comprises:
a receiver member including at least one limiter; and
an insert member including at least one catch,
wherein the receiver member and the insert member are configured to telescopingly mate with one another,
wherein the insert member comprises an opening configured to receive a pin,
wherein the receiver comprises a channel configured to engage the pin, and
wherein the pin is configured to travel within the channel to constrain movement of the receiver member relative to the insert member prior to the catch engaging the limiter so that receiver and insert remain in an interconnected state, and
wherein the compression member is configured to allow a dynamic range of compression such that the length of the compression member can increase or decrease following an initial amount of static compression.

11. The system of claim 10, wherein the compression device is capable of changing from a first length to a second length following compression of the device.

12. The system of claim 10, wherein the receiver member includes one or more apertures to receive fasteners and the insert member includes one or more apertures to receive fasteners.

13. The system of claim 12, wherein the receiver member includes two or more limiters and the insert member includes two or more catches, each catch configured to engage an associated limiter.

14. The system of claim 10, wherein the receiver member includes one or more grooves that engage one or more rails of the insert member.

15. The system of claim 14, wherein the one or more grooves and the one or more rails are slidably connected and configured to reduce uneven engagement of the receiver member and the insert member.

16. The system of claim 10, wherein the limiter contains a projecting surface.

17. The system of claim 16, wherein the projecting surface is resiliently connected to the receiver.

18. The system of claim 10, wherein the system further comprises graft material that is packed into the intervertebral device.

* * * * *